US008186217B2

(12) United States Patent
Veltink

(10) Patent No.: US 8,186,217 B2
(45) Date of Patent: May 29, 2012

(54) DEVICE AND METHOD FOR MEASURING THE DYNAMIC INTERACTION BETWEEN BODIES

(75) Inventor: Petrus Hermanus Veltink, Haaksbergen (NL)

(73) Assignee: Xsens Technology B.V., Enschede (NL)

(*) Notice: Subject to any disclaimer, the term of this patent is extended or adjusted under 35 U.S.C. 154(b) by 720 days.

(21) Appl. No.: 12/200,763

(22) Filed: Aug. 28, 2008

(65) Prior Publication Data
US 2009/0056445 A1    Mar. 5, 2009

(30) Foreign Application Priority Data

Aug. 29, 2007 (NL) ..................................... 2000835

(51) Int. Cl.
G01P 15/00 (2006.01)
(52) U.S. Cl. ....................................... 73/489; 73/514.01
(58) Field of Classification Search .............. 73/514.01, 73/493, 514.33, 514.32, 514.34, 489, 490, 73/510, 511
See application file for complete search history.

(56) References Cited

U.S. PATENT DOCUMENTS

| 5,581,484 | A | 12/1996 | Prince | |
| 6,516,284 | B2 * | 2/2003 | Flentov et al. | 702/142 |
| 6,836,744 | B1 * | 12/2004 | Asphahani et al. | 702/141 |
| 7,223,624 | B2 * | 5/2007 | Wu et al. | 438/52 |
| 7,320,253 | B2 * | 1/2008 | Hanazawa et al. | 73/862.042 |
| 7,322,236 | B2 * | 1/2008 | Combi et al. | 73/488 |
| 7,467,060 | B2 * | 12/2008 | Kulach et al. | 702/141 |
| 7,610,166 | B1 * | 10/2009 | Solinsky | 702/160 |
| 2005/0172717 | A1 | 8/2005 | Wu et al. | |
| 2006/0053908 | A1 * | 3/2006 | Ishigami et al. | 73/866.1 |
| 2007/0032748 | A1 * | 2/2007 | McNeil et al. | 600/595 |
| 2007/0289380 | A1 * | 12/2007 | Lin et al. | 73/493 |
| 2008/0312565 | A1 * | 12/2008 | Celik-Butler et al. | 601/43 |
| 2009/0007661 | A1 * | 1/2009 | Nasiri et al. | 73/504.03 |

FOREIGN PATENT DOCUMENTS

EP    1 561 724 A1    10/2005
JP    205268758 A    9/2005

OTHER PUBLICATIONS

Veltink, P.H., Kortier, H.G., Schepers ,H.M, Sensing Dynamic Interaction With the Environment, Proceedings of Annual Symposium of the IEEE/EMBS Benelux chapter, Dec. 6-7, 2007, Heeze, NL, p. 13.
Veltink, P.H., Kortier, H.G., Schepers, H.M., Sensing Dynamic Interaction With the Environment, Conference Book, International Conference on Ambulatory Monitoring of Physical Activity and Movement, May 21-24, 2008, Rotterdam, NL, p. 167.

(Continued)

Primary Examiner — Helen C. Kwok
(74) Attorney, Agent, or Firm — Miller, Matthias & Hull LLP

(57) ABSTRACT

The invention relates to a device for measuring the dynamic interaction, in particular power transfer and work performed, between a first and a second body, in particular during relatively random movements. The device comprises a housing in which at least one kinematic sensor and at least one kinetic sensor is arranged, in addition to processing means for processing the signals from the sensors, and communication means for data exchange with the outside world. The invention also relates to a method for measuring the dynamic interaction between a first and a second body, and a carrier provided with a number of devices according to the invention.

16 Claims, 2 Drawing Sheets

OTHER PUBLICATIONS

Schepers, H.M.. Koopman, J.M., Veltink, P.H., Ambulatory Assessment of Ankle and Foot Dynamics, IEEE Transactions on Biomedical Engineering, vol. 54, No. 5, May 2007 (pp. 895-902).
Kai, Makoto et al, Use of an Instrument Sandwiched Between the Hoof and Shoe to Measure Vertical Ground Reaction Forces and Three-Dimensional Acceleration at the Walk, Trot, and Canter in Horses, AJVR, vol. 61, No. 8, Aug. 2000 (pp. 979-985).
Veltink, P.H., "BSc EL/BMT:Powersensor", Internet Artikel, [Online], XP002481379, obtained from the Internet at: URL:http://bss.ewi.utwente.nl/education/occupied/biomechatronics/powersenor_doc/index.html> (1 page).
Search Report and Written Opinion for Netherlands Patent Application No. 2000835 (May 23, 2008).
Student Assignment Description, "Power Sensor" (Mar. 5, 2007).

* cited by examiner

DEVICE AND METHOD FOR MEASURING THE DYNAMIC INTERACTION BETWEEN BODIES

FIELD OF THE INVENTION

The invention relates to a device and method for measuring the dynamic interaction between a first and a second body. The invention relates particularly to a device and method for measuring the dynamic interaction between a first and a second body during relatively random movements. The invention further relates to a miniature device for measuring the dynamic interaction between a first and a second body.

BACKGROUND OF THE INVENTION

Devices are known from the prior art for analyzing the human running movement. Kinematic sensors, such as for instance inertial sensors (accelerometers, angular velocity sensors) and magnetometers, are used for this purpose. Devices are also known which can determine the transfer of forces between two bodies. Kinetic sensors such as for instance pressure sensors, force sensors and moment sensors are used here. A known method makes use of so-called force plates. Such plates provided with a plurality of force sensors are arranged on the surface. A test subject then steps onto the force plate, whereby the force plate is dynamically loaded. From the measured forces information is obtained about the interaction between the surface (force plate) and test subject. During running on a relatively hard surface the reaction forces of the surface and the acceleration of the foot do not generally equal zero simultaneously. When the foot is situated on the hard surface, the velocity of the foot will be substantially zero, while the reaction force will on the other hand differ from zero. When the foot is not situated on the surface, the reverse phenomenon occurs: the velocity of the foot will not equal zero while the measured reaction force is zero. That is, during running on a relatively hard surface no power is transferred from the foot to the surface, except possibly during the impact phase when the foot touches the surface during the transition from swing to standing phase.

There are however also circumstances which can be envisaged where power is transferred by means of a movement of a body, in particular of a human body. Power is thus produced for instance during all kinds of physical work, wherein objects are manipulated, or during sporting activity. At the moment there is no adequate device and method available which is able to measure the dynamic interaction between a first and a second body during relatively random movements, and in particular the power transfer from a first body to a second body. The ability to measure the interaction between two or more bodies during relatively random movements, for instance between the body of a sportsperson and a ball or between the body of the sportsperson and a preferably non-hard surface, provides useful information about the movement, about the forces and about the power transferred by the sportsperson to the ball or to the surface. Such information can be used to improve the performance of the sportsperson. Such information can also be of great value in ergonomics (the evaluation of physical load during work) and for disabled persons who use a prosthesis.

The present invention has for its object to provide a device and method for measuring the dynamic interaction between a first and a second body, particularly during relatively random movements.

BRIEF SUMMARY OF THE INVENTION

In one aspect of the invention, a device is provided for measuring the dynamic interaction between a first and a second body, which device comprises a housing in which at least one kinematic sensor and at least one kinetic sensor is arranged, in addition to processing means for processing the signals from the sensors, and communication means for data exchange with the outside world.

BRIEF DESCRIPTION OF THE DRAWINGS

While the appended claims set forth the features of the present invention with particularity, the invention and its advantages are best understood from the following detailed description taken in conjunction with the accompanying drawings, of which:

DETAILED DESCRIPTION OF THE INVENTION

Figure 1:
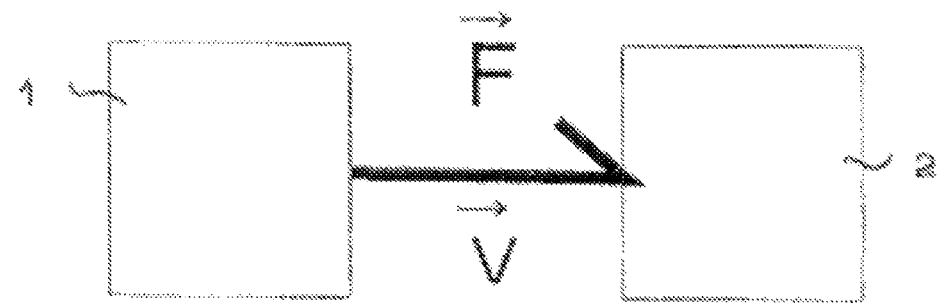
FIG. 1 shows schematically the interaction between a first and a second body, in accordance with an embodiment of the invention.

The following examples further illustrate the invention but, of course, should not be construed as in any way limiting its scope.

An embodiment of the invention provides a device which comprises a housing in which at least one kinematic sensor and at least one kinetic sensor is arranged, in addition to processing means for processing the signals from the sensors, and communication means for data exchange with the outside world. By placing the device between the contact surface of the first in the second body, and because the device is provided with at least one kinematic sensor and at least one kinetic sensor, it becomes possible to directly determine the power transferred via the contact surface.

It is noted that devices are known from the prior art which are able to determine the power transfer between two bodies. A known example is a cycle provided with a force sensor on the crankshaft, and a rotation velocity sensor on for instance the pedal shaft. Such a device is however only able to estimate the power transfer between two bodies (a person and the cycle) for a limited series of movements, in the present case a pedaling movement. Such a movement is imposed by the first and/or the second body, and is therefore not random but is already substantially predetermined. The device according to an embodiment of the invention on the other hand makes it possible to obtain an estimation of the power transfer between two bodies performing relatively random movements, such as is the case for instance between a ball and a hand gripping thereon. In the context of the present application a relatively random movement is understood to mean any movement which, although aimed by the first and/or the second body (for instance by the muscular power of the sportsperson), is in principle not predetermined.

The device according to an embodiment of the invention comprises kinematic and kinetic sensors for measuring respectively velocity and force. The processing means of the device according to an embodiment of the invention receive, for instance when the first and second body enter into contact, the force signals generated by the kinetic sensors and the velocity and/or angular velocity signals generated by the kinematic sensors. By estimating the velocity from the movement signals—if desired at any moment—and subsequently calculating the internal vector product from the force and velocity signal (represented in the moving coordinate system of the sensor) a direct, if desired continuous measurement of the transferred power is obtained. This is because a first body comes into contact with a second body, and the power produced by the first body at a random point in time t is then given by the internal vector product of the measured force vector F and the measured velocity vector v in the same coordinate system:

$$P(t)=F(t).v(t) \quad (1)$$

When the force vectors $F(x_i)$ and the velocity vectors $v(x_i)$ are measured at different positions $x_i$ of a contact surface, the power at a determined point in time is then calculated by adding together the internal vector products at all positions:

$$P(t)=\Sigma F(x_i,t).v(x_i,t) \quad (2)$$

Each pair of force and velocity vectors must be represented in a random, possibly moving coordinate system. This coordinate system may differ for different pairs of force and velocity vectors. The vectors can thus be expressed in the moving local coordinate system of the device. If, in addition to linear forces and velocities, rotational moments $M(x_i, t)$ and angular velocities $\omega(x_i, t)$ are also measured, the above stated formulae (1) and (2) can then be further supplemented by including therein the (sum of the) internal vector products $\Sigma M(x_i, t).\omega(x_i,t)$.

In order to be able to determine the transferred power, a precise estimation of the velocity is preferably made. The velocity vector can be estimated according to an embodiment of the invention by integrating through time the movement acceleration a derived from an acceleration sensor. An acceleration sensor measures the sum $s_a$ of the movement acceleration a and the gravitational acceleration g:

$$s_a=a-g \quad (3)$$

Because the gravitational acceleration g is always directed vertically, the movement acceleration a can be derived from the measured signal $s_a$ by adding the gravitational acceleration g thereto. For this purpose the inclination of the acceleration sensor (the angle of the sensor relative to the vertical) must preferably also be estimated. In the case of relatively small movement accelerations the inclination can be estimated from the signals from the acceleration sensor, which is then used as inclinometer. This procedure is known per se and is described extensively in H. J. Luinge, P. H. Veltink, Inclination Measurement of human movement using a 3-D accelerometer with autocalibaration, IEEE Transactions on Neural Systems and Rehabilitation Engineering, vol. 12, 2004, pp. 112-121, which is incorporated by reference in its entirety herein for everything that it teaches. The signals can be low-pass filtered at a desired cut-off frequency. It is also possible to apply a Kalman filter. In the case of greater movement accelerations the inclination can be estimated by fusing the information derived from a triaxial acceleration sensor and a triaxial angular velocity sensor. This also per se known procedure is described for instance in H. J. Luinge, P. H. Veltink, Measuring Orientation of Human Body Segments Using Miniature Gyroscopes and Accelerometers, Medical and Biological Engineering and Computing, vol. 43, 2005, pp. 273-282, which is incorporated by reference in its entirety herein for everything that it teaches. The device according to embodiments of the invention is distinguished from the prior art by, inter alia, the linking of movement information and the force information in the same sensor in order to estimate power transfer and to characterize the dynamics of the body.

In order to make the measurement more accurate and simpler, the device according to an embodiment of the invention is further characterized in that the at least one kinematic sensor and the at least one kinetic sensor are situated at mutually predetermined fixed positions, and preferably at relatively small mutual distance, in the housing. This ensures that the measured and/or estimated forces and velocities, and optionally rotational moments and angular velocities, are measured in the same coordinate system. This is because in this preferred variant the sensors have a fixed position and orientation relative to a coordinate system connected to the device. With knowledge of the movement of the device the measured quantities can then be converted by means of per se known transformations into a global coordinate system connected to the fixed world in which the device is located. What must be understood by a relatively small distance is determined by the movement: the mutual distance of the sensors must be so small in the present preferred variant that it need not be taken into account in the calculations. In this preferred variant the sensors must therefore be situated effectively at the same position. This also requires relatively small sensor systems.

In another preferred embodiment the device is characterized in that the at least one kinematic sensor and/or the at least one kinetic sensor are triaxial sensors. In determined cases it is possible to measure a considerable part of the power transfer using uniaxial and/or optionally biaxial sensors, although use of triaxial sensors has the advantage that substantially the whole power transfer between the bodies can be measured.

Because the contact between the invented device and the first and/or second body can last a relatively short time, a relatively high sample frequency of the measured signals is preferably applied during the contact. This enhances a more accurate measurement of the interaction between the first and second body. A preferred embodiment of the device according to the invention comprises sensors with a sample frequency which can be temporarily increased during contact between the two bodies (when the interaction force does not equal zero), and a buffer unit for the measured signals.

According to one embodiment of the invention the device is preferably a miniature device. In such a miniature device, for instance in the form of a chip, the sensors are preferably arranged in or between two plates which make contact with both bodies. The kinetic sensors are preferably arranged in this miniature device such that they form the connection between upper and lower plate. Force and/or moment signals are derived from the deformation of this connection, measured with for instance resistance strain gauges and/or capacitance displacement sensors. The kinematic sensors are preferably positioned such that they are substantially not influenced, or only to a limited extent, by mechanical deformations. They are preferably coupled for this purpose to upper or lower plate.

In a preferred variant the device according to an embodiment of the invention preferably also comprises at least one triaxial angular velocity sensor. Using such a triaxial angular velocity sensor (or gyroscope) an accurate estimation of the three-dimensional orientation of the device can be determined, whereby the movement acceleration a can be derived at all times from the acceleration sensor signals $s_a$.

The device according to an embodiment of the invention can be utilized as separate measuring unit if desired. It is however advantageous that a number of devices according to another embodiment of the invention are combined by being arranged in a carrier suitable for the purpose. Suitable carriers comprise for instance a body suit, preferably provided with shoes or other parts for the body parts which make physical contact with the fixed world, such as hands, feet, back, pelvis and so on. A particularly suitable carrier takes the form of a glove. Such a glove is simple to arrange and can map a large number of interactions between human body and objects of diverse nature. Devices with kinetic and kinematic sensors as described above are preferably incorporated in this embodiment variant at all contact points between body part (hand) and object, so that the whole interaction force is measured. This whole interaction force can be determined by adding together the forces measured with all devices in one shared sensor system, possibly the global coordinate system of the fixed world. The relative orientations of the sensor devices must preferably be determined for this purpose. This determination can be made from the movement information measured with the kinematic sensors of the sensor devices, as already described above.

Alternatively or additionally hereto, information about the relative orientation of the sensors can be obtained when the angular velocities and mutual differences in acceleration of the sensor devices are sufficiently small. This is for instance the case with a hand. Under these conditions it can be assumed that the relative accelerations of the sensor devices relative to each other are small compared to the overall acceleration. On this premise it can be assumed that the triaxial acceleration sensors measure the same acceleration in all sensor devices at any point in time, only in a different coordinate system. The direction of the vectorial acceleration sensor signal at any moment gives for each device partial information about the relative orientations of the devices. If the direction of this acceleration varies sufficiently during a movement, the whole relative orientations of the sensor devices can moreover be determined. This is only possible if the relative orientations of the sensor devices and the hand/body segments to which they are attached do not change appreciably before the acceleration has been measured in a number of directions.

An embodiment of the invention likewise relates to a method for measuring the power transfer from a first body to a second body, and in particular for measuring the power transfer during relatively random movements. In the invented method at least one device as described above is arranged on the first and/or second body, and the power is obtained by calculating the internal vector product of the force signals generated by the kinetic sensors and the velocity signals generated by the kinematic sensors with the processing means of at least one device. The advantages of the method are already described above in respect of the description of the device, and will therefore not be repeated here.

It is advantageous to characterize the method in that the devices according to an embodiment of the invention are arranged at substantially each contact position between the first and second body. This is possible in excellent manner by incorporating the devices in a carrier, such as preferably a glove.

The surface properties of the contact surface between first and second body can be important in the method according to an embodiment of the invention. For some configurations, wherein shear forces are undesirable or desirable to limited extent, a surface with a low friction is preferably provided while, conversely, for other configurations in which it must be possible to transfer shear forces a surface with a high friction is preferably applied. The method according to an embodiment of the invention preferably comprises a step in which the surface properties of the first and/or second body are adapted or chosen for the purpose of realizing the desired interaction between the two bodies.

According to an embodiment of the invention the work performed by the first body for a determined time is obtained by integrating over this time the internal vector products of the force signals generated by the kinetic sensors and the velocity signals generated by the kinematic sensors. As is known, small errors in the estimation of sensor offset can result in appreciable integration errors, also referred to as integration drift, particularly in the case of integration over a longer period of time. In order to minimize these integration errors, and thereby improve the estimation of the work performed, it is desirable to utilize knowledge about starting and end conditions in respect of velocity, position, orientation and power and/or knowledge about average velocities, positions, orientations and/or powers and/or the possibly approximate knowledge of the cyclic character of a movement in order to minimize estimation errors in sensor offset and/or to utilize information about the duration of the interaction in order to minimize the duration of the integration.

The method and device according to an embodiment of the invention find excellent application in determining the power transfer between at least two bodies. It is however also possible to obtain information from the obtained sensor signals about the dynamic properties of the bodies. In the context of the present application dynamic properties are understood to mean the relation between movement of and force on the body during a dynamic load. Properties such as mass, stiffness and damping as well as other properties are an important factor here. In a preferred embodiment of the method information about the dynamic properties of the second, and possibly also the first, body is determined from force signals generated by the kinetic sensors and the velocity signals generated by the kinematic sensors, which sensors are arranged between the two bodies, this by means of recursive identification. In such a method a mathematical model is made of the dynamic properties of the body, or use is made of such a model. No fixed value is however given to the model parameters (the actual values of stiffness, damping, mass and so on) in the model. For a determined set of parameter values the force at the measured movement or relevant movement quantities at the measured force are then calculated, and this is compared to the measured quantities. The parameter values are then adapted such that the difference between calculated and measured quantities is minimized. The dynamic properties of the first and/or of the second body can thus be determined. It is noted that such a recursive identification is per se known, although not in the present combination with a direct power measurement. It must be noted in addition that in the interaction between two dynamic bodies only a partial characterization of the dynamic properties of each of the bodies can generally be obtained, since the interaction force and joint movement of the contact surface must comply with the dynamic characteristics of both bodies, and for this reason and due to the limited joint movements that are performed, both bodies are possibly not sufficiently excited in the whole operational range of each of the bodies. The relation between measured force and movement information can nevertheless result in many cases in a usable characterization of the dynamics of one or both bodies.

The device and method according to embodiments of the invention can be used for many purposes. It is thus possible to use them in movement monitoring systems in general, and in particular in sport, for instance in the analysis of the power, force and movement and the relations between these quantities when throwing a ball, a discus, arrows, when striking with a tennis racket or golf club, during skating, where the device is arranged for instance in the skate, during rowing, football (contact foot/ball) and the like. The measurement can here be used to improve the performance of the athlete. Another possible application is the measurement of power in ergonomics, wherein the interaction between the human body and a tool, chair and so on is determined. The device is also suitable for diverse medical applications and in rehabilitation, for instance in the testing and optimizing of prostheses, and in order to monitor and/or improve the interaction between a robot and its environment.

Referring to FIG. 1, a first body 1 and a second body 2 are shown schematically. First body 1 can for instance be a (part of a) human body, or a robot. Second body 2 can for instance be a tool or the surface or a projectile such as for instance a ball. The interaction between the two bodies (1, 2) can take place by transfer of forces F and/or moments M from first body 1 to second body 2 (and of course vice versa). If the two bodies moreover have at the location where interaction force and movement is measured a velocity v or angular velocity ω not equal to zero, a power P is then transferred which is given by the internal vector product of the force vector and the velocity vector (according to formula (1)) and, in the case of moment/angular velocity, the internal vector product of moment vector and angular velocity vector added thereto.

Figure 2:
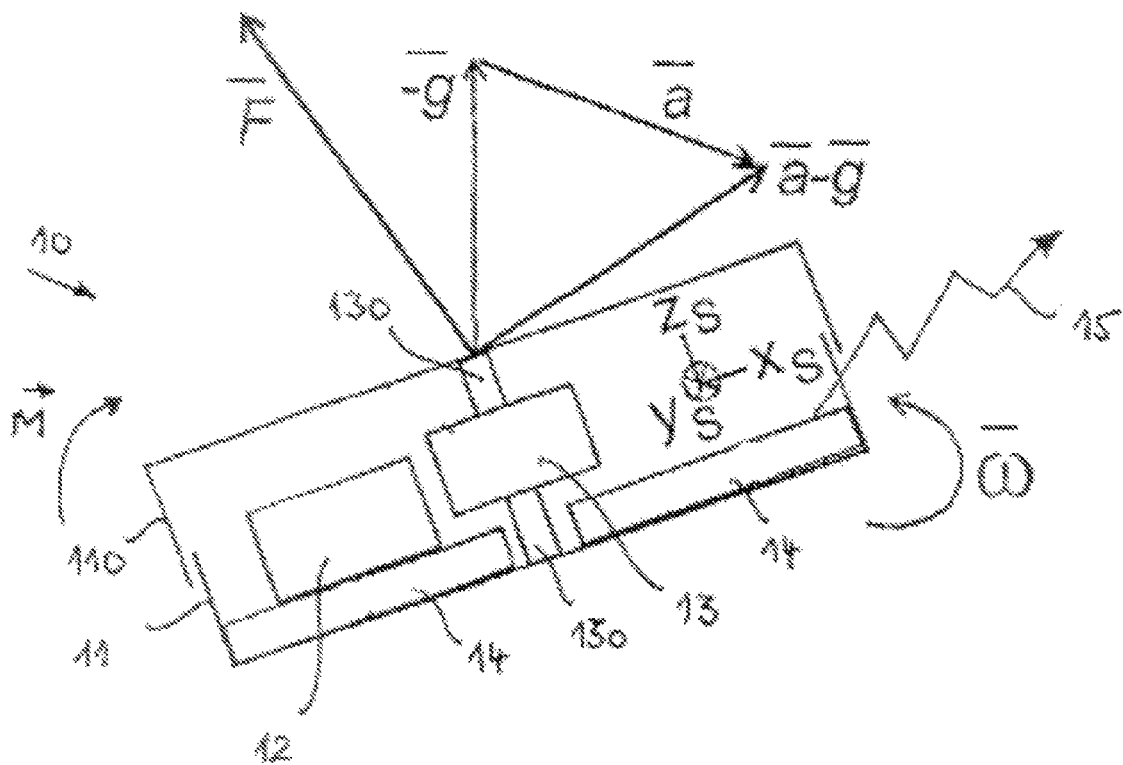
FIG. 2 shows schematically a first exemplary embodiment of the device according to the invention.

FIG. 2 shows an exemplary embodiment of a device 10 for measuring the dynamic interaction, and in particular the power transfer, between first body 1 and second body 2. Device 10 comprises a housing 11 in which at least one kinematic sensor 12 and at least one kinetic sensor 13 are arranged, preferably of the triaxial type. Kinetic sensor(s) 13 are connected via mechanical connections 130 to both parts of housing 11. The kinematic sensor(s) are attached to one of the two parts of the housing, particularly to a displaceable part 110 of housing 11. Upper and lower parts of the housing form the contact plates for the two bodies. Housing 11 is likewise provided with per se known processing means 14 (electronics, processors and the like) for the purpose of processing the signals from the sensors (12, 13). If desired, housing 11 also comprises communication means 15 for data exchange with the outside world. In the shown embodiment variant communication means 15 take a wireless form, for instance by means of radio waves. The sensors (12, 13) are situated at mutual predetermined fixed positions in housing 11, preferably at a relatively short distance from each other. They form a relatively rigid whole with housing 11. The force and acceleration signals from sensors (12, 13) are thus measured in a coordinate system ($x_s$, $y_s$, $z_s$) connected to device 10. According to an embodiment of the invention the power transfer from first body 1 to second body 2 is estimated in the case of relatively random movements by arranging at least one device 10 on first body 1 and/or on second body 2 and/or between both bodies. Devices 10 are hereby loaded by forces F, and possibly by rotational moments M. Because at least one of the bodies (1, 2) is also in motion, devices 10 will also be subjected to a velocity v, and possibly a rotation velocity ω. The power is obtained by calculating the internal vector product of the force and/or rotational moment signals generated by kinetic sensors 13, and by calculating the velocity and/or rotation velocity signals generated by kinematic sensors 12 with processing means 14 of devices 10 or with processing means of a remote system which receives the signals via the communication provision of device 10.

Figure 4:
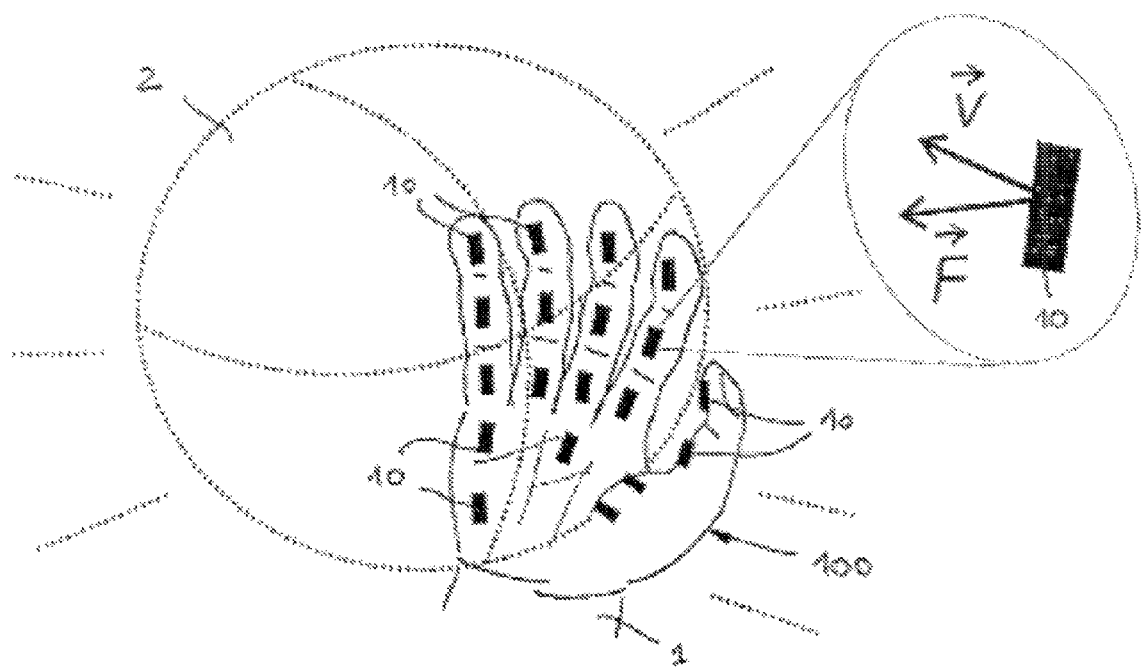
FIG. 4 finally shows schematically a carrier provided with a number of devices, according to an embodiment of the invention.

If measurement is taking place simultaneously with a plurality of devices 10, it is then advantageous to arrange these in a carrier. Referring to FIG. 4, a carrier is shown in the form of a glove 100. Glove 100 is provided on the palm side with a number of devices 10 according to an embodiment of the invention. As shown, the devices can be arranged on the palm of the hand itself, but also on for instance the finger phalanges. Glove 100 is arranged on the hand of a person, wherein the hand thus functions as first body 1. The power transfer from first body 1 to a second body, such as for instance a ball 2, can be determined in very simple and accurate manner with the glove 100 provided with devices 10. As shown in FIG. 4, it is important when positioning devices 10 on the glove that they preferably be placed such that they are arranged at substantially every possible contact position between hand 1 and ball 2. If this is not the case, part of the power transfer can then be "missed". In the method according to an embodiment of the invention the work performed by hand 1 for a determined time is obtained by adding together and integrating over this time the internal vector products of the force and velocity signals measured by all devices 10 which have come into contact with ball 2.

Figure 3:
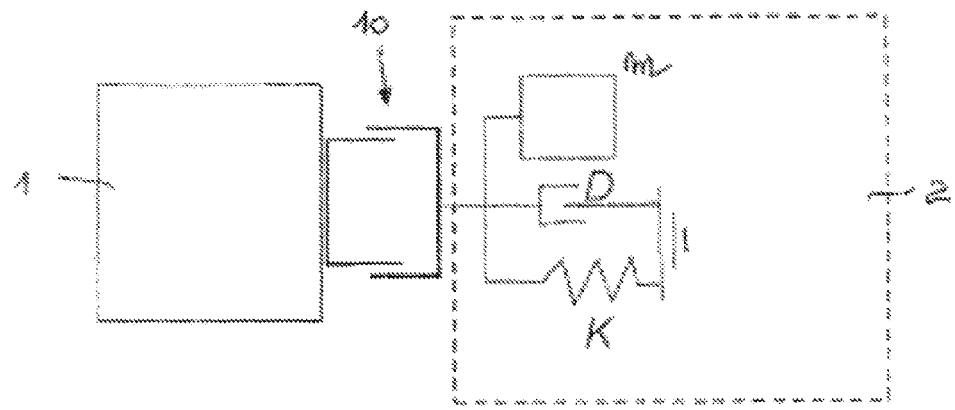
FIG. 3 shows schematically a first exemplary embodiment of the method according to the invention.

It is also possible according to an embodiment of the invention to determine partial or complete information about the dynamic properties of the ball or other body 2 from the force signals generated by kinetic sensors 13 and the velocity signals generated by kinematic sensors 12 per device 10. Such a determination is shown schematically in FIG. 3. Shown is a first body 1 which is in contact with a second body 2. A device 10 as according to FIG. 2 is situated between the two bodies (1, 2). The dynamic properties of second body 2 are represented schematically by a number of parameters, such as the mass m, stiffness K and damping D. It will be apparent that, if desired, these parameters can be supplemented with other parameters relevant to the dynamic behaviour of second body 2. The dynamic properties of second body 2 can be determined from the force and velocity signals generated by device 10 by means of recursive identification or other algorithms suitable for this purpose. A mathematical model is here made of the dynamic properties of second body 2. No fixed value is given in the model to the model parameters m, K and D. The movement is then calculated at the measured force (or vice versa) for a determined set of parameters values, and this is compared to the measured force or movement. The parameter values are then adapted such that the difference between calculated and measured movement/force is minimized. The dynamic properties of the second, and possibly also the first, body can thus be at least partially determined. Once the dynamic properties of the second body have been determined, they can be used, on the basis of a measurement of the transferred power, to separate the energy imparted to second body 2 into imparted potential energy and kinetic energy. This, and the information obtained about the dynamic characteristics of body 2, makes it possible to determine the path of second body 2 (for instance if this body is a ball 2) once it has been released from first body 1.

It will be apparent that the invention is not limited to the exemplary embodiments shown and described here, but that within the scope of the appended claims variants are possible which will be self-evident to the skilled person in this field.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A device for measuring a dynamic interaction between a first and a second body by measuring power transfer from the first body to the second body, the device comprising a housing in which at least one kinematic sensor and at least one kinetic sensor are arranged, in addition to a processing means for processing signals which transmit data from the sensors, and a communication means for data exchange with a receiver which is not part of the device and is remotely located from the device.

2. The device of claim 1, wherein the at least one kinematic sensor and the at least one kinetic sensor are situated at mutually predetermined fixed positions and relative orientations in the housing.

3. The device of claim 2, wherein the at least one kinematic sensor and the at least one kinetic sensor are situated at relatively small distance from each other in the housing.

4. The device of claim 1, wherein the at least one kinematic sensor and the at least one kinetic sensor are triaxial sensors.

5. The device of claim 1, wherein the device is a miniature device.

6. The device of claim 1, wherein the housing comprises a first and a second side which are mutually connected by means of a substantially rigid but deformable connection, wherein the at least one kinetic sensor is arranged in the connection and the at least one kinematic sensor is attached to one of the first and second side.

7. The device of claim 1 further comprising at least one triaxial acceleration sensor, one or more of at least one triaxial force sensor and at least one triaxial angular velocity sensor, and at least one triaxial moment sensor.

8. The device of claim 1 further comprising a carrier.

9. The device of claim 8, wherein the carrier is a glove.

10. A method for measuring a power transfer from a first body to a second body, wherein at least one device is arranged on at least one of the first and second bodies, and the power is obtained by calculating, using processor of the at least one device or of an external machine with which the device may communicate, an internal vector product of force signals generated by at least one kinetic sensor and velocity signals generated by at least one kinematic sensor; and obtaining work performed by the first body for a determined time by integrating over this time the internal vector product of the force signals generated by the at least one kinetic sensor and velocity signals generated by the at least one kinematic sensor, the at least one device comprising a housing in which the at least one kinematic sensor and the at least one kinetic sensor are arranged and a communication means for data exchange with a receiver which is not part of the device and is remotely located from the device.

11. The method of claim 10, wherein at least two devices are arranged on at least one of the first and second body, and overall power is obtained by adding together transferred powers for all devices.

12. The method of claim 10 further comprising measuring the power transfer from the first body to the second body during relatively random movements.

13. The method of claim 10, wherein the at least one device is arranged at substantially every contact position between the first and second body.

14. The method of claim 10, wherein knowledge about starting and end conditions and other preconditions, and duration of an interaction between the two bodies is used in order to minimize integration errors.

15. The method of claim 10, wherein the relative orientations of forces and velocities of a plurality of devices with kinematic and kinetic sensors placed at the interface of at least one of the first and second body are estimated by assuming that the measured kinematic quantities are equal at all times for all devices, but are only represented in another coordinate system.

16. The method of claim 10, wherein dynamic properties of at least one of the first and second body are at least partially determined from the force signals generated by the at least one kinetic sensor and the velocity signals generated by the at least one kinematic sensor via recursive identification.

* * * * *